(12) United States Patent
McArdle et al.

(10) Patent No.: US 9,481,640 B2
(45) Date of Patent: Nov. 1, 2016

(54) ELECTRON DEFICIENT OLEFINS

(71) Applicant: Henkel IP & Holding GmbH, Duesseldorf (DE)

(72) Inventors: Ciaran McArdle, Dublin (IE); Ligang Zhao, Duesseldorf (DE); Stefano L. Gherardi, Dublin (IE); Kevin D. Murnaghan, Duesseldorf (DE)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 14/945,843

(22) Filed: Nov. 19, 2015

(65) Prior Publication Data

US 2016/0075641 A1    Mar. 17, 2016

Related U.S. Application Data

(63) Continuation of application No. 14/663,722, filed on Mar. 20, 2015, which is a continuation of application No. 12/766,457, filed on Apr. 23, 2010, which is a continuation of application No. PCT/EP2008/064490, filed on Oct. 24, 2008.

(60) Provisional application No. 60/982,157, filed on Oct. 24, 2007.

(51) Int. Cl.

| | |
|---|---|
| C08F 20/10 | (2006.01) |
| C07C 255/23 | (2006.01) |
| C07C 69/602 | (2006.01) |
| C08F 20/42 | (2006.01) |
| C07C 255/17 | (2006.01) |
| C07C 69/73 | (2006.01) |
| C07C 255/15 | (2006.01) |
| C07C 69/593 | (2006.01) |
| C07C 255/19 | (2006.01) |
| C08F 222/14 | (2006.01) |
| C08F 222/30 | (2006.01) |
| C08K 5/13 | (2006.01) |

(52) U.S. Cl.
CPC ........... *C07C 255/17* (2013.01); *C07C 69/593* (2013.01); *C07C 69/73* (2013.01); *C07C 255/15* (2013.01); *C07C 255/19* (2013.01); *C07C 255/23* (2013.01); *C08F 222/14* (2013.01); *C08F 222/30* (2013.01); *C08K 5/13* (2013.01)

(58) Field of Classification Search
CPC .... C07C 69/73; C07C 255/15; C07C 255/23
See application file for complete search history.

(56) References Cited

U.S. PATENT DOCUMENTS

| | | |
|---|---|---|
| 2,363,464 A | 11/1944 | Senkus |
| 2,413,249 A | 12/1946 | Senkus |
| 2,413,250 A | 12/1946 | Senkus |
| 2,415,046 A | 1/1947 | Senkus |
| 2,582,128 A | 1/1952 | Hurwitz |
| 2,721,858 A | 10/1955 | Joyner et al. |
| 2,756,251 A | 7/1956 | Joyner et al. |
| 2,763,677 A | 9/1956 | Jeremias |
| 2,870,193 A | 1/1959 | Pollack et al. |
| 3,048,615 A | 8/1962 | Fields |
| 3,142,698 A | 7/1964 | Halpern et al. |
| 3,221,745 A | 12/1965 | Coover, Jr. et al. |
| 3,282,773 A | 11/1966 | Wicker, Jr. et al. |
| 3,554,987 A | 1/1971 | Smith |
| 3,903,055 A | 9/1975 | Buck |
| 3,975,422 A | 8/1976 | Buck |
| 3,988,299 A | 10/1976 | Malofsky |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,056,543 A | 11/1977 | Ponticello |
| 4,160,864 A | 7/1979 | Ponticello et al. |
| 4,202,920 A | 5/1980 | Renner et al. |
| 4,364,876 A | 12/1982 | Kimura et al. |
| 4,440,910 A | 4/1984 | O'Connor |
| 4,512,357 A | 4/1985 | Earl |
| 4,556,700 A | 12/1985 | Harris et al. |
| 4,560,723 A | 12/1985 | Millet et al. |
| 4,582,648 A | 4/1986 | Hirakawa |
| 4,587,059 A | 5/1986 | Harth et al. |
| 4,622,414 A | 11/1986 | McKervey |
| 4,636,539 A | 1/1987 | Harris et al. |
| 4,695,615 A | 9/1987 | Leonard et al. |
| 4,718,966 A | 1/1988 | Harris et al. |
| 4,764,545 A | 8/1988 | Yosida |
| 4,837,260 A | 6/1989 | Sato et al. |
| 4,855,461 A | 8/1989 | Harris |

(Continued)

FOREIGN PATENT DOCUMENTS

| | | |
|---|---|---|
| CA | 2027985 A1 | 4/1991 |
| DE | 2626173 A1 | 12/1977 |

(Continued)

OTHER PUBLICATIONS

V. Vuayalakshmi et al., "Synthesis, Characterization and Evaluation of Alkyl 2-Bromoacrylates as Adhesives," Eur. Polym. J., vol. 29, No. 10, pp. 1323-1328 (1993).

Carl J. Buck, "Unequivocal Synthesis of Bis(2-Cyanoacrylate) Monomers," I. Via Anthracene Adducts, Journal of Polymer Science, Polymer Chemistry Edition, vol. 16, 2475-507 (1978).

G. Jones, "The Knoevenagel Condensation," Organic Reactions, vol. XV, 204, Wiley New York (1967).

F. Bigi et al., "Montmorillonite KSF as an Inorganic Water Stable, and Reusable Catalyst for the Knoevenagel Synthesis of Courmarin-3-carboxylic Acids," Journal Organic Chemistry, vol. 64, 1033-35 (1999).

(Continued)

*Primary Examiner* — Peter F Godenschwager
(74) *Attorney, Agent, or Firm* — Steven C. Bauman

(57) ABSTRACT

This invention relates to novel electron deficient olefins, such as certain 2-cyanoacrylates and methylidene malonates, prepared using an imine or an iminium salt.

6 Claims, 3 Drawing Sheets

(56) References Cited

U.S. PATENT DOCUMENTS

| | | | |
|---|---|---|---|
| 4,876,045 | A | 10/1989 | Longo et al. |
| 4,906,317 | A | 3/1990 | Liu |
| 5,142,098 | A | 8/1992 | Bru-Magniez et al. |
| 5,288,794 | A | 2/1994 | Attarwala |
| 5,306,752 | A | 4/1994 | Attarwala |
| 5,312,864 | A | 5/1994 | Wenz et al. |
| 5,328,944 | A | 7/1994 | Attarwala et al. |
| 5,340,873 | A | 8/1994 | Mitry |
| 5,359,101 | A | 10/1994 | Woods et al. |
| 5,386,047 | A | 1/1995 | Nakos et al. |
| 5,424,343 | A | 6/1995 | Attarwala |
| 5,424,344 | A | 6/1995 | Lewin |
| 5,455,369 | A | 10/1995 | Meier et al. |
| 5,624,699 | A | 4/1997 | Lang |
| 5,703,267 | A | 12/1997 | Takahashi et al. |
| 5,744,642 | A | 4/1998 | Lantzsch et al. |
| 5,994,464 | A | 11/1999 | Ohsawa et al. |
| 6,093,780 | A | 7/2000 | Attarwala |
| 6,096,848 | A | 8/2000 | Gololobov et al. |
| 6,174,919 | B1 | 1/2001 | Hickey |
| 6,245,933 | B1 | 6/2001 | Malofsky et al. |
| 6,291,544 | B1 | 9/2001 | Kotzev |
| 6,531,460 | B1 | 3/2003 | Takenouchi et al. |
| 6,743,858 | B2 | 6/2004 | Hickey et al. |
| 6,833,196 | B1 | 12/2004 | Wojciak |
| 6,835,789 | B1 | 12/2004 | Kneafsey et al. |
| 2006/0094833 | A1 | 5/2006 | McDonnell et al. |
| 2006/0269870 | A1 | 11/2006 | Harada et al. |
| 2008/0241249 | A1 | 10/2008 | Quintero et al. |

FOREIGN PATENT DOCUMENTS

| | | | |
|---|---|---|---|
| DE | 4034080 | A1 | 6/1991 |
| DE | 19519958 | A1 | 12/1995 |
| EP | 0127855 | A1 | 12/1984 |
| EP | 0267982 | A1 | 5/1988 |
| EP | 0459617 | A1 | 12/1991 |
| JP | S59222462 | | 12/1984 |
| JP | 11106372 | | 4/1999 |
| JP | 2003507494 | A | 2/2003 |
| WO | 9415590 | A1 | 7/1994 |
| WO | 9415907 | A1 | 7/1994 |
| WO | 9532183 | A1 | 11/1995 |
| WO | 9914206 | A1 | 3/1999 |
| WO | 0112243 | | 5/2000 |
| WO | 03006225 | A1 | 1/2003 |
| WO | 03086605 | A2 | 10/2003 |

OTHER PUBLICATIONS

B. Green et al., Synthesis of Steroidal 16, 17-Fused Unsaturated Lactones, Journal Organic Chemistry, vol. 50, 640-44 (1985).
P. Rao et al., "Zinc Chloride As A New Catalyst for Knoevenagel Condensation," Tetrahedron Letters, vol. 32, No. 41, 5821-22 (1991).
J.S. Yadav et al., "Phosphane-Catalyzed Knoevenagel Condensation: A Facile Synthesis of Cyanoacrylates and α-Cyanonitriles," European Journal Organic Chemistry, 546-51 (2004).
L. Tietze et al., Comprehensive Organic Synthesis, Pergamon Press, Oxford, vol. 2, Chapter 1.11, 341 (1991).
P. Laszlo, "Catalysis of Organic Reactions by Inorganic Solids," Accounts of Chemical Research, vol. 19, 121-27 (1986).
K. Kloestra et al., "Base and Acid Catalysis by the Alkali-containing MCM-41 Mesoporous Molecular Sieve," Journal Chemical Soc. Chem. Commun., 1005-06 (1995).
P. Lednor et al., "The Use of a High Surface Area Silicon Oxynitride as a Solid, Basic Catalyst," Journal Chemical Society Chem. Commun., 1625-26 (1991).
F. Bigi et al., "A Revision of the Biginelli Reaction Under Solid Acid Catalysis. Solvent-free Synthesis of Dihydropyrimidines Over Montmorillonite KSF," Tetrahedron Letters, vol. 40, 3465-68 (1999).
F. Bigi et al., "Clean synthesis in water: uncatalysed preparation of ylidenemalononitriles," Green Chemistry, vol. 2, 101-03 (2000).
R. Breslow "Hydrophobic Effects on Simple Organic Reactions in Water," Accounts of Chemical Research, vol. 24, 159-64 (1991).
C. Li, "Organic Reactions in Aqueous Media—With a Focus on Carbon-Carbon Bond Formation," Chemical Reviews, vol. 93, 2023-35 (1993).
T. Welton, "Room Temperature Ionic Liquids. Solvents for Synthesis and Catalysis," Chemical Reviews vol. 99, 2071-83 (1999).
D. Morrison et al., "Base-promoted reactions in ionic liquid solvents. The Knoevenagel and Robinson annulation reactions," Tetrahedron Letters, vol. 42, 6053-55 (2001).
Fraga-Dubreuil et al., "Grafted ionic liquid-phase-supported synthesis of small organic molecules," Tetrahedron Letters, vol. 42, 6097-6100 (2001).
M. Smietana et al., "Preparation of Silyl Enol Ethers Using (Bistrimethylsilyl)acetamide in Ionic Liquids," Organic Letters, vol. 3, No. 7, 1037-39 (2001).
Li et al., "n-Butyl Pyridinium Nitrate as a Reusable Ionic Liquid Medium for Knoevenagel Condensation," Chinese Chemical Letters, vol. 14, No. 5, 448-50 (2003).
J. Harjani et al., "Lewis acidic ionic liquids for the synthesis of electrophilic alkenes via the Knoevenagel condensation," Tetrahedron Letters, vol. 43, 1127-30 (2002).
Xu et al., "Knoevenagel condensation reaction catalyzed by functionalized ionic liquid 1-(2-Hydroxyethyl)-3-methyl imidazolium chloride," Chinese Journal of Organic Chemistry, vol. 24(10), 1253-56 (2004).
Su et al., "Organic Reactions in Ionic Liquids: Knoevenagel Condensation Catalyzed by Ethylenediammonium Diacetate," Synthesis 2003, No. 4, 555-59 (2003).
Moehrle et al., "Aminomethylierung von. 1, 3-Diketonen," Pharmazie, vol. 40, 697-701 (1985).
J. Mar., "Reactions," Advanced Organic Chemistry, 3rd Edition, Wiley & Sons Inc., 417 (1985).
J. Mar., "Addition to Carbon-Hetero Multiple Bonds," Advanced Organic Chemistry, 3rd Edition, Wiley & Sons, 802-03 (1985).
M.B. Smith, Organic Synthesis, McGraw Hill International Chemistry Series, 1302 (1994).
Tehrani et al., "Product Class 8: Iminium Salts," Science of Synthesis, vol. 27, 313-48 (2004).
B. Hin et al., "Facile Synthesis of a-Substituted Acrylate Esters," Journal of Organic Chemistry, vol. 67, 7365-68 (2002).
Holy et al, "The Mannich Reaction-II Derivatization of Aldehydes and Ketones Using Dimethyl(methylene)ammoniumum Salts," Tetrahedron Letters, vol. 35, 613-19 (1979).
Bryson et al, "Preformed Mannich Salts: A Facile Preparation of Dimethyl(methylene)ammonium Iodide," Journal of Organic Chemistry, vol. 45, 524-25 (1980).
J. Mar. et al., The Pinacol Rearrangement, Advanced Organic Chemistry, 3rd Edition, Wiley & Sons, 963-64 (1985).
J. Mar., "Free-Radical Substitution," Advanced Organic Chemistry, 3rd Edition, Wiley & Sons, 642 (1985).
Jahn et al., "A Novel and Simple Method for the Preparation of Iminium Salts," Tetrahedron Letters, vol. 34, No. 37 5863-66 (1993).
R.J. Vijn et al., Sythesis, 573 (1994).
Davis, "Chemistry Letters," vol. 33, Issue 9, 1072-77 (2004).
Davis et al., "Ionic Liquids in Synthesis," P. Wasserscheld and T. Welton, eds., Wley-VCH Verlag GmbH & Co. KGaA, Chapter 2 (2002).
M.G. Djamali et al., "Synthese und Eigenschaften eines Celluloseaustauschers mit Diaminodibenzo-18-Krone-6 als Ankergruppe," Die Angewandte Makromolecular Chemie, vol. 92, 145-54 (1980).
K. Babic, "Reactive and Functional Polymers," vol. 66, 1494-1505 (2006).
Trumbo et al., "Copolymerization Behavior of 3-Isopropenyl-α,α-Dimethylbenzylamine and Preliminary Evaluation of the Copolymers in Thermoset Coatings," Journal of Applied Polymer Science, vol. 82, 1030-39 (2001).

(56) References Cited

OTHER PUBLICATIONS

T. Giesenberg et al., "Synthesis and Functionalization of a New Kind of Silica Particle," Angew. Chem. Int. Ed., 43, 5697-5700 (2004).
Zhang et al., "An Investigation of Knoevenagel condensation reaction in microreactors using a new zeolite catalyst," Applied Catalysis A: General, 261, 109-118 (2004).
Mehnert et al., "Chemical Communications," 3010 (2002).
Lee and Lee, "Bulletin of the Korean Chemical Society," vol. 25, Issue 10, 1531-37 (2004).
H.R. Snyder and W.E. Hamlin, "Alkylation of Nitroparaffins with Amines and their Derivatives," Journal of American Chemical Society, vol. 72, 5082-85 (1950).
H.G. Johnson, "Reaction of Aliphatic Amines with Formaldehyde and Nitroparaffins. II. Secondary Amines," Journal of American Chemical Society, vol. 68, 12-14 (1946).
M. Semkus, "Journal of the American Chemical Society," vol. 68, 10-12 (1946).
Sarac, "Progress in Polymer Science," vol. 24, 1149-1201 (1999).
Brough et al., "Pyrimidinyl Nitronyl Nitroxides," Chemical European Journal, vol. 12, 5134 (2006).
Zhou et al., J. Polym. Sci., Part A Polym. Chem. Ed., 29, 1097 (1991).
Mehrotra et al., "Journal of Organometallic Chemistry," vol. 24, 611-21 (1970).
Son et al., "Synthesis of Hexahydro-3,3,5,5,7-pentaalkyl-2H-1,4-diazepin-2-ones from 1,3-Diamenes and Ketones," J. Org. Chem., vol. 46, 323 (1981).
Senkus, Acetals of Nitro Alcohols and Corresponding Amino Acetals, J. Amer. Chem. Soc., vol. 69, 1380-81 (1947).
Renner et al., "Cure of Epoxy Resins with Esters of Cyanoacrylic Acid," Journal of Polymer Science: Polymer Chemistry Edition, vol. 23, 2341 (1985).
Kennedy et al., "Macromers by Carboncationic Polymerization. X. Synthesis, Characterization, and Polymerizability of Cyanoacrylate-Capped Polyisobutylenes," Journal of Macromolecular Science, Part A, 28:2, 209-24 (1991).
Khrustalev et al., "Synthesis and X-ray structural study of 1-adamantylmethy 2-cyanoacrylatel and 1,10-decanediol bis-2-cyanoacrylate," Russian Chemical Bulletin, vol. 45, No. 9, 2172 (1996).
Y. Gololobov et al., "A novel approach to the synthesis of bis(2-cyanoacrylates)," Russian Chemical Bulletin, vol. 42, No. 5, 961 (1993).
Y. Gololobov et al., "Synthesis of bis(2-cyanoacrylates) from 2-cyanoacryloyl chloride and 2-butene-and 2-butyne-1,4-diols," Russian Chemical Bulletin, vol. 44, No. 4, 760 (1995).
J.-L. De Keyser et al., "A Versatile and Convenient Multigram Synthesis of Methylidenemalonic Acid Diesters," J. Org. Chem., vol. 53, 4859 (1986).
Vijayalakshmi et al., "Alkyl and substituted alkyl 2-cyanoacrylates. Part I. Synthesis and Properties," J. Adhesion Science Technology, vol. 4, No. 9, 733 (1990).
Guseva et al., "Organic Chemistry. Synthesis of functionally substituted cyanoacetates," Russian Chemical Bulletin, vol. 42, No. 3, 478 (1993).
Guseva et al., "Organic Chemistry" Russian Chemical Bulletin, vol. 43, No. 4, 595 (1995).
Gololobov and Gruber, Russian Chemical Review, vol. 66, Issue 11, 953 (1997).
Senchenya et al., "Silicon-containing esters of a-cyanoacrylic acid: synthesis and properties," Russian Chemical Bulletin, vol. 42, No. 5, 909 (1993).
Bowie J. H. et al., "Tetrahedron," vol. 23, 305-20 (1967).
J. S. Norwick et al., J. Org. Chem., 57(28), 7364-66 (1992).
International Search Report for International Application No. PCT/EP2008/064489 dated Dec. 30, 2008.
International Search Report for International Application No. PCT/EP2008/064490 dated May 4, 2009.
International Search Report for International Application No. PCT/EP2008/064488 dated Jul. 16, 2009.
H.C. Haas et al., "Carbamylmethyl Esthers of Unsaturated Acids," Journal of Polymer Science: vol. XXXVII, Issue 131; pp. 317-319; 1959, (XP002518680).
J.-L. De Keyser et al., "A Versatile and Convenient Multigram Synthesis of Methylidenemalonic Acid Diesters," J. Org. Chem., pp. 4859-4862, (1988) (XP002518681).
D.A. Aronovich et al.; J. Appl. Chem. USSR.; vol. 52, pp. 900-902; 1979 (XP002518682).
X. Yang; Organic Preparations and Procedures International; vol. 30, No. 2; pp. 239-242; 1998 (XP002518684).
P.H. Mason et al., "A New Route to Substituted Glutaric Acid Derivatives From Allylic Malonates," Synthetic Communications; vol. 25(2); pp. 183-190; 1995.
T. Sato et al., "Synthesis of Copper (II) Chelate of ethyl a-(acetoacetoxymethyl)acrylate and its Radical-Initiated Polymerization," Makromol. Chem., Rapid Commun. vol. 11; pp. 553-557; 1990.
M.L. Meketa et al., "An efficacious method for the halogenation of .beta.-dicarbonyl compounds under mildly acidic conditions," Tetrahedron Letters; vol. 46(28); pp. 4749-4751; 2005, XP002520970.
M.L. Meketa et al., "An efficacious method for the halogenation of .beta.-dicarbonyl compounds under mildly acidic conditions," Tetrahedron Letters; vol. 46(28); pp. 4749-4751; 2005, XP002520971.
R.C. Cookson, et al., "2-Phenylthioallyl Alcohols and Their Use in the Synthesis of 1,4-Diketones and Cyclopentenones," Journal of Chemical Society, Chemical Communications; (23) p. 990; 1976, XP002520969.
P.H. Mason et al., "Some Mechanistic and Synthetic Aspects of the DABCO Catalyzed Rearrangement of Allylic Esters," Tetrahedron, vol. 50(41);pp. 12001-12008, XP002520967.
L.S. Boguslayskaya et al., Journal of Organic Chemistry; vol. 9; pp. 295-299; 1793, XP002520972.
Samatha et al., "Effect of Addition of Various Acrylates on the Performance of Ethyl Cyanoacrylate Adhesive," Polym.—Plast. Technol. Eng., 39(2), 381-92 (2000).
Vijayalakshmi et al., "Synthesis and End Use Evaluation of Pinene-based Alicyclic Acrylates," J. Polym. Mat., 13, pp. 127-131 (1996).
Yamada et al., "Determination of Absolute Rate Constants for Radical Polymerization and Copolymerization of Ethyl a-Cyanoacrylate in the Presence of Effective Inhibitors against Anionic Polymerization," Makromol. Chem., 184, 1025 (1983).
Vijayalakshmi et al., "Synthesis of 3-Substituted-2-cyanoacrylates: Their Evaluation as Cross-link in Cyanoacrylate Adhesive Compositions," J. Polym. Mat., 49, 1387 (1993).
Ponticello, "The Preparation of a-Substituted Acrylic Esters," J. Polym. Sci., Polym. Chem. Edn., 17, pp. 3509-3518 (1979).
Pines, Alul and Kolobielski, "Bromination of a-Methylstyrene with N-Bromosuccinimide, Synthesis of 2-Phenyl-1,5-hexadiene," J. Org. Chem., 22, 1113 (1957).

ELECTRON DEFICIENT OLEFINS

BACKGROUND OF THE INVENTION

1. Field of the Invention

This invention relates to novel electron deficient olefins, such as certain 2-cyanoacrylates or methylidene malonates, prepared using an imine or an iminium salt.

2. Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624, 699, 4,364,876, 2,721,858, 2,763,677 and 2,756,251.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci., Polym. Chem. Ed.*, 16, 2475-2507 (1978), and U.S. Pat. Nos. 3,975,422, 3,903,055, 4,003,942, 4,012,402, and 4,013,703].

A variety of other processes for producing cyanoacrylate monomers are known, some of which are described below. For instance, U.S. Pat. No. 5,703,267 defines a process for producing a 2-cyanoacrylic acid which comprises subjecting a 2-cyanoacrylate and an organic acid to a transesterification reaction.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a poly(ethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermolyzing the oligomeric intermediate product for a period of time sufficient to effect its conversion to monomeric 2-cyanoacrylates.

Commercial production of cyanoacrylate monomers ordinarily relies on the depolymerisation of a prepolymer formed under Knoevenagel condensation reaction conditions, as noted above. Still today the Knoevenagel condensation reaction is believed to remain the most efficient and prevalent commercial method for producing high yields of monofunctional cyanoacrylates. Nevertheless, it would be desirable to not have to resort to thermally induced depolymerisation of a prepolymer produced by the Knoevenagel condensation reaction. This prospect may also enable facile access to highly useful difunctional monomers, such as so-called biscyanaocrylates or hybrid materials of cyanoacrylate and other polymerisable or reactive functionality.

For instance, cyanoacrylate esters bearing moisture, base, acid, thermally sensitive or otherwise reactive moieties, may not be conveniently produced and isolated under Knoevenagel reaction conditions.

While methods describing the preparation of cyanoacrylates with reactive functionality in the ester side chain (such as biscyanoacrylates) are known (see e.g. Buck and U.S. Pat. Nos. 3,975,422, 3,903,055, 4,003,942, 4,012,402, and 4,013,703), the cyanoacrylates with reactive functionality in the ester side chain are prepared in a multi-step process involving protective group strategies and functional group transformations to arrive at adducts which must subsequently be deprotected to yield cyanoacrylates with additional functionality. The same approach has been described to arrive at a cyanoacrylate-capped polyisobutylene by Kennedy et al., *J. Macromol Sci. Chem.*, A28, 209 (1991).

A transesterification approach to achieve cyanoacrylates with reactive functions in the ester side chain has also been described in U.S. Pat. No. 6,096,848, in which cyanoacrylate esters, previously made by Knoevenagel reaction, are hydrolysed in strong acid conditions in the presence of a difunctional alcohol to yield biscyanoacrylates. The method described in the '848 patent requires long reaction times, copious volumes of solvent and solvent switching methods to isolate the bifunctional cyanoacrylates free from acid stablisers in modest to low yields [see also Khrustalev et al., *Russian Chem. Bull.*, 45, 9, 2172 (1996)].

An alternative approach to the preparation of cyanoacrylates with reactive functions in the ester side chain uses cyanoacrylic acid or its acid chloride (cyanoacryloyl chloride). See e.g. International Patent Publication Nos. WO 94/15590A1, WO 94/115907A1, and WO 95/32183A1, and U.S. Pat. No. 5,703,267.

The use of cyanoacrylic acid and cyanoacryloyl chloride to arrive at cyanoacrylates has also been described in Y. Gololobov and I. Chernoglazova, *Russian Chem. Bull.*, 42, 5, 961 (1993) and Y. Gololobov and M. Galkina, *Russian Chem. Bull.*, 44, 4, 760 (1995). These methods require flash vacuum pyrolysis techniques conducted in quartz tubes at high temperatures (approximately 600° C.) and exposure of highly reactive, polymerisable intermediate materials to chemical reactions with highly acidic and moisture sensitive reagents.

With regard to the preparation of other types of electron deficient olefins with reactive functionality, U.S. Pat. No. 5,142,098 describes a copper catalysed reaction of malonates and formaldehyde to form methylidenemalonate monomers that are trapped in situ by a "diene" anthracene in a Diels-Alder reaction. The '098 patent describes a diester adduct of anthracene, that is a precursor for a methylidenemalonate monomer with one ethyl ester and one glycidyl ester. The '098 patent indicates that reaction—a retro Diels- Alder thermolysis step—was not successful for the preparation of the particular methylidene malonate bearing the glycidyl functionality in the ester side chain. The retro Diels-Alder reaction has been reported as useful in the syntheses of other methylidene malonates (see e.g. J-L. De Keyser et al., *J. Org. Chem.*, 53, 4859 (1988)).

Accordingly, it will be appreciated that the preparation of electron deficient olefins, such as 2-cyanoacrylates or methylidene malonates, with a reactive functional group in the ester, or even with large or bulky groups in the ester side chain, is not a trivial matter.

As a result and because of the limitations of the hitherto known various processes for cyanoacrylate synthesis and the sensitivity of the novel electron deficient olefins, such novel electron deficient olefins have not been described to date. Until now.

SUMMARY OF THE INVENTION

Unlike the state of the technology, the present invention provides novel electron deficient olefins, such as 2-cyanoacrylates or methylidene malonates, with a reactive functional group in the ester side chain, prepared using an imine or an iminium salt.

The novel compounds are electron deficient olefins within structure I:

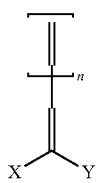

where X is (a) an electron withdrawing group, or (b) Y;
Y is

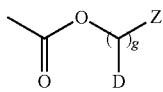

where D is selected from H, alkyl or aryl,
Z is either
(i)

where Q is
  a. an electron withdrawing group (such as CN, $CO_2R$, $CO_2H$, COCl, COR, $COPO(OR)_2$, $COPOR_2$, $SO_2R$, $SO_3R$ or $NO_2$) or
  b. a first reactive functionality, or
  (ii) a second reactive functionality,
  g is 1-10; and
  n is 0 or 1.
Desirably, g is 1. However, if g>1, D should be H.

More specifically, the inventive compounds are embraced by structure II

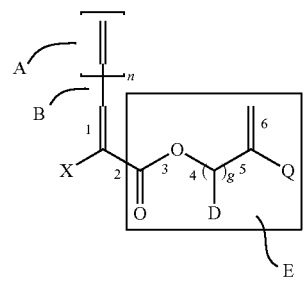

where X is an electron withdrawing group or E, E is as shown,

is a reactive functionality, D is selected from H, alkyl or aryl, n is 0 or 1, and A, B, 1, 2, 3, 4, 5, and 6 are each references to bond designations.

In an alternative aspect the inventive compounds are embraced by structure III

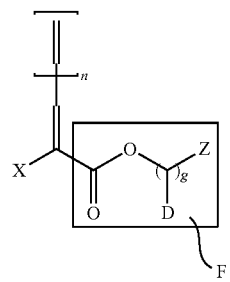

where X is an electron withdrawing group or F, D is selected from H, alkyl or aryl, Z is a reactive functionality, n is 0 or 1 and g is 1. The reactive functionality of Z in structure III may be selected from epoxides, episulfides, oxetanes, thioxetanes, dioxolanes, dioxanes, isocyanates, maleimides, oxazolines, succinimides, 2-cyanoacrylates, methylidene malonates, acrylonitrile, (meth)acrylates, carboxylic acids and derivatives thereof, cyanoacetates, methylene malonates, hydroxyls, silanes, siloxanes, titanates, or zirconates.

The present invention also provides compositions of the compounds of structures I, together with a stabilizer package comprising at least one of a free radical stabilizer and an anionic stabilizer; and optionally, one or more additives selected from cure accelerators, thickeners, thixotropes, tougheners, thermal resistance-conferring agents, or plasticizers.

The present invention further provides compositions of the compounds of structures I, II or III, together with a cyanoacrylate or a methylidene malonate. Or the present invention further provides compositions of certain of the compounds of structures I, II or III, together with a coreactant, such as one selected from epoxides, episulfides, oxetanes, thioxetanes, dioxolanes, dioxanes, isocyanates, maleimides, oxazolines, (meth)acrylates, cyanoacrylates, methylidene malonates or vinyl ethers.

DETAILED DESCRIPTION OF THE INVENTION

Figure 1:
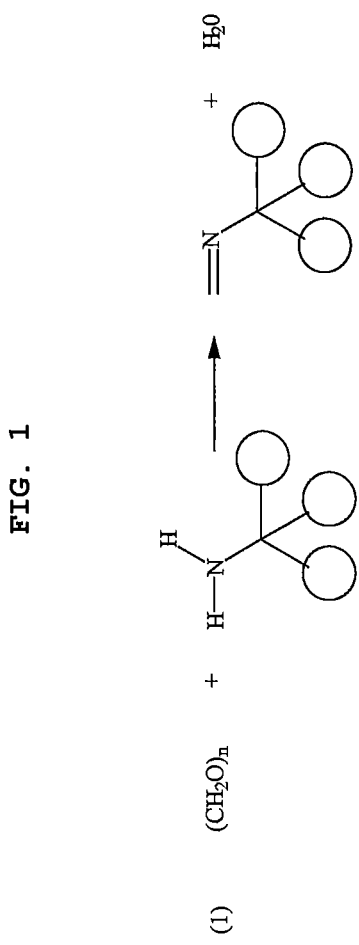
FIG. 1 depicts a synthetic scheme by which iminium salts may be prepared.

As noted above, the present invention provides electron deficient olefins within structure I:

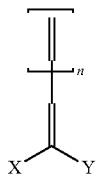
I where X is (a) an electron withdrawing group, or (b) Y;
Y is

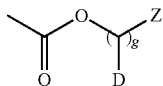

where D is selected from H, alkyl (such as one to twenty carbon atoms) or aryl (such as six to twenty carbon atoms),
Z is either
  (i)

where Q is
  a. an electron withdrawing group (such as CN, $CO_2R$, $CO_2H$, COCl, COR, $COPO(OR)_2$, $COPOR_2$, $SO_2R$, $SO_3R$ or $NO_2$) or
  b. a first reactive functionality, or
  (ii) a second reactive functionality,
g is 1-10; and
n is 0 or 1.
Desirably, g is 1. However, if g>1, D should be H.

More specifically, the inventive compounds are embraced by structure II

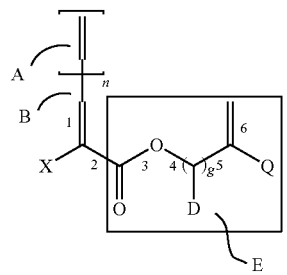
II where X is an electron withdrawing group (such as CN, $CO_2R$, $CO_2H$, COCl, COR, $COPO(OR)_2$, $COPOR_2$, $SO_2R$, $SO_3R$ or $NO_2$, where R is $C_{1-4}$) or E, E is as shown,

is a reactive functionality, D is selected from H, alkyl or aryl, n is 0 or 1, and A, B, 1, 2, 3, 4, 5, and 6 are each references to bond designations. Q may be an amide or thioamide embraced by

C(T)NUV, where T is O or S and U or V are each independently selected from H or R, where R is $C_{1-4}$. In addition, in structure II, the vinyl group labeled '6' is disposed 6 bond lengths distance from the vinyl group labeled '1', ignoring side branches and where Q is not H.

In an alternative aspect the inventive compounds are embraced by structure III

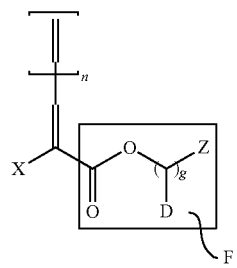
III where X is an electron withdrawing group (such as CN, $CO_2R$, $CO_2H$, COCl, COR, $COPO(OR)_2$, $COPOR_2$, $SO_2R$, $SO_3R$ or $NO_2$, where R is $C_{1-4}$) or F, D is selected from H, alkyl (such as one to twenty carbon atoms) or aryl (such as six to twenty carbon atoms), Z is a reactive functionality, n is 0 or 1 and g is 1. The reactive functionality of Z in structure III may be selected from epoxides, episulfides, oxetanes, thioxetanes, dioxolanes, dioxanes, isocyanates, maleimides, oxazolines, succinimides, 2-cyanoacrylates, methylidene malonates, acrylonitrile, (meth)acrylates, carboxylic acids and derivatives thereof, cyanoacetates, methylene malonates, hydroxyls, silanes, siloxanes, titanates, or zirconates.

Representative examples of novel electron deficient olefins within the scope of the invention include

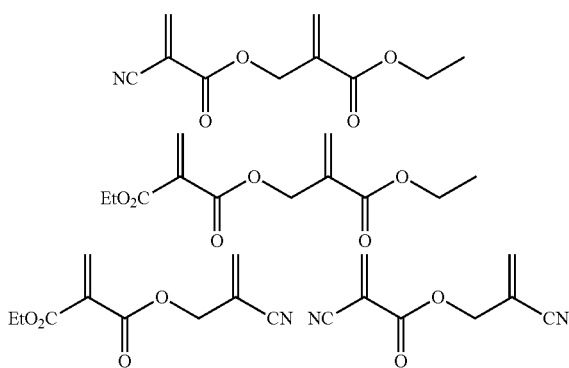

To prepare such compounds in accordance with the present invention, one may use imines embraced by structure VI or iminium salts embraced by structure VII.

The imine embraced within structure VI is as follows:

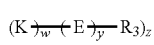
                           VI where K is

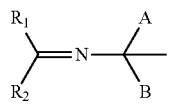

where in this connection $R_1$-$R_2$ are each independently selected from hydrogen, alkenyl (such as two to twenty carbon atoms), or alkynyl (such as two to twenty carbon atoms); and A-B are each independently selected from linear, branched, or cyclic alkyl (such as three to twenty carbon atoms) or alkenyl (such as three to twenty carbon atoms) which may be interrupted with heteroatoms or substituted by functional groups, or A and B taken together form a cyclic or polycyclic alkyl or alkenyl structure, which may be interrupted with heteroatoms or substituted by functional groups;

E is selected from a linear, branched or cyclic hydrocarbon with or without one or more nitrogen-containing substituents thereon, a heterocyclic, an aromatic or an organosiloxane group or part thereof or linkage; and $R_3$ in this connection is selected from a hydrocarbon, a heterocyclic, an aromatic or an organosiloxane group or linkage;

w is 1-100; y is 1-100 and z is 0-100.

When more than one of K, E or $R_3$ are present, each instance thereof is defined independently from the other instance(s).

The imine more specifically is embraced within structure VIA as follows:

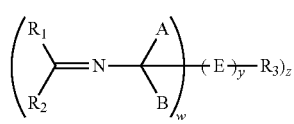
                           VIA where in this connection $R_1$-$R_2$, A-B, E, $R_3$, w, y and z are as defined above.

The iminium salt embraced within structure VII is as follows:

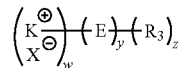
                           VII where K is

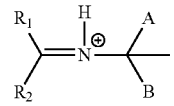

where in this connection $R_1$-$R_2$ are each independently selected from hydrogen, alkenyl, or alkynyl; and A-B are each independently selected from linear, branched, or cyclic alkyl or alkenyl which may be interrupted with heteroatoms or substituted by functional groups, or A and B taken together form a cyclic or polycyclic alkyl or alkenyl structure, which may be interrupted with heteroatoms or substituted by functional groups;

E is selected from a linear, branched or cyclic hydrocarbon with or without one or more nitrogen-containing substituents thereon, a heterocyclic, an aromatic or an organosiloxane group or part thereof or linkage; and $R_3$ in this connection is selected from a hydrocarbon, a heterocyclic, an aromatic or an organosiloxane group or linkage;

w is 1-100; y is 1-100 and z is 0-100; and

X is an anion.

When more than one of K, E or $R_3$ are present, each instance thereof is defined independently from the other instance(s).

The iminium salt is embraced more specifically by structure VIIA as follows:

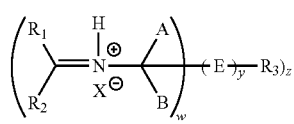
                           VIIA where in this connection $R_1$-$R_2$, A-B, E, $R_3$, w, y and z, and X are as defined above.

The imine in some cases may be an imine having an onium salt, such as an ammonium or amine salt functionality. In some cases the imines may be termed an "ionic liquid" (or "IL") or a task specific ionic liquid (or, "TSIL"), as will be discussed in more detail below. Likewise, the iminium salts may be termed an "ionic liquid" (or "IL") or a task specific ionic liquid (or, "TSIL"), as will be discussed in more detail below.

In such cases where the imine of structure VI or the iminium salt of structure VII is particularly stable at room temperature conditions when in the presence of the precursor to the electron deficient olefin, a modest amount of heat may be useful to allow the reaction to generate electron deficient olefins. Exposure to elevated temperature conditions is particularly desirable with iminium salts of structure VII.

Reference to the figures may be useful to appreciate further how electron deficient olefins of the present invention are prepared, which is described in more detail below and in the Examples section that follows thereafter.

Thus, as an initial reactant, is an aldehyde compound having the structure $R_3R_4C=O$, where $R_3$ is hydrogen and $R_4$ is a hydrogen, vinyl or propargyl. The aldehyde compound may be an aldehyde itself or a source of an aldehyde, such as one that yields an aldehyde like formaldehyde under appropriate reaction conditions. The aldehyde compound in a desirable embodiment includes formaldehyde or a source thereof, such as paraformaldehyde (see FIG. 1), formalin, or 1,3,5-trioxane, or vinyl aldehydes, such as acrolein.

As a reactant with such an aldehyde is a primary amine. Primary amines attached to a carbon bearing no alpha protons are particularly desirable, such as t-alkyl primary amines. Rohm and Haas Co., Philadelphia, Pa. has sold commercially for a number of years a series of t-alkyl primary amines, which are designated as PRIMENE-brand amines.

For instance, t-alkyl primary amines available from Rohm and Haas include PRIMENE 81-R and PRIMENE JM-T. These PRIMENE-brand t-alkyl primary amines have highly branched alkyl chains (represented schematically by circle symbols in the Figures for simplicity) in which the amino nitrogen atom is attached directly to a tertiary carbon. These t-alkyl primary amines consist of mixtures of isomeric amines, with PRIMENE 81-R consisting of an isomeric mixture with $C_{12}$-$C_{14}$ carbon branches and having an average molecular weight of 185 and PRIMENE JM-T consisting of an isomeric mixture with $C_{16}$-$C_{22}$ carbon branches and having average molecular weight of 269.

PRIMENE MD, also known as menthanediamine (1,8-diamino-p-menthane) or (4-amino-α,α-4-trimethyl-cyclohexanemethanamine, CAS No. 80-52-4), is a primary alicyclic diamine, in which both amino groups are attached to tertiary carbon atoms. Like other alicyclic t-alkyl primary amines, menthanediamine is somewhat less reactive than similar straight chain diamines. Yet another PRIMENE, PRIMENE TOA has tertiary octyl chains and a molecular weight of 129. In the examples given below, PRIMENE 81-R MSA iminium salt, formed in reaction (2) of FIG. 1, is used.

Figure 2:
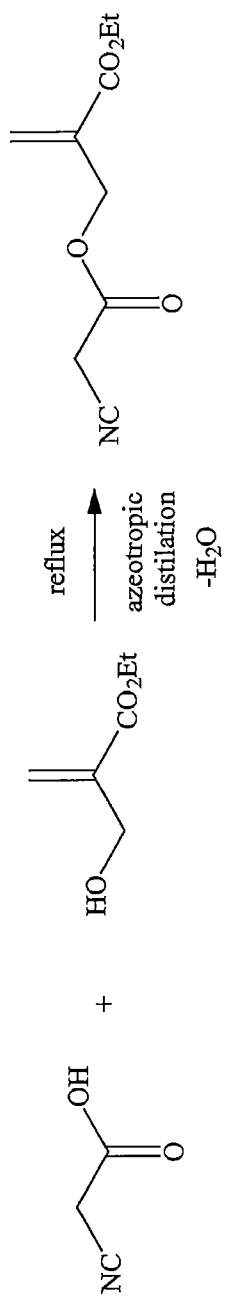
FIG. 2 depicts a synthetic scheme by which a precursor to an inventive electron deficient olefin may be prepared.
Figure 3:
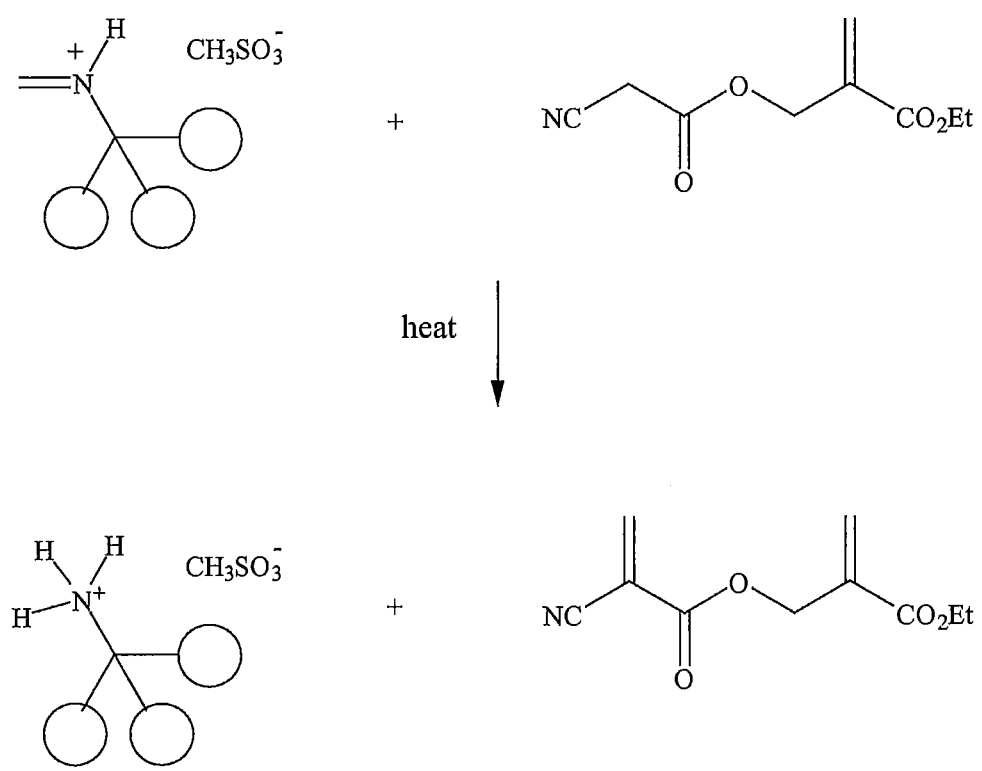
FIG. 3 depicts a synthetic scheme by which the precursor to an inventive electron deficient olefin (from FIG. 2) is used with the iminium salt (from FIG. 1) to form the inventive electron deficient olefin.

The imines, whether or not bearing ammonium salt functionality or whether or not they are tethered to a support, are then reacted with compounds containing a methylene linkage having at least one, desirably two, electron withdrawing substituent(s) attached thereto. The preparation of a methylene compound useful as a precursor to an electron deficient olefin is depicted in FIG. 2, which illustrates the esterification of cyanoacetic acid with alpha hydroxymethyl acrylate. In these compounds, the electron withdrawing substituent is selected from nitrile, carboxylic acids, carboxylic esters, sulphonic or suphinic acids or their esters, ketones, phosphocarbonyl, or nitro. Such compounds are reacted with iminium salts for example as depicted in FIG. 3 to form novel electron deficient olefins. In a desirable embodiment, these compounds have two or more electron withdrawing substituents, which may be the same or different, such as nitrile and carboxylic acid ester—in this case, a cyanoacrylate. Of course, the reactivity of these compounds in large part depends on the degree of electron withdrawing capability of the particular substituent, and the number of substituents on the active methylene carbon.

The reaction to form the novel electron deficient olefins may proceed with or without heating or cooling, depending of course on the specific reactants and the scale of the reaction. Decomposition of the source of formaldehyde, e.g., paraformaldehyde, may occur under gentle heating up to a temperature of about 70° C., to liberate formaldehyde in situ in the reaction medium. The temperature may be reached through an external heating element or internally by means of the exotherm that may be generated, depending of course on the identity of the reactants. The temperature of the reaction should be controlled however to accommodate any such exothermic processes.

The time of reaction may be monitored by reference to the formation of the desired novel electron deficient olefin product. A $^1$H NMR spectrometer is a particularly useful tool in this regard. The time of reaction may be as little as 1 minute, for instance, or longer or shorter for that matter depending again on the identity of the specific reactants, the scale of the reaction and whether heat is introduced to or removed from the reaction conditions.

Once formed, the novel electron deficient olefin may be isolated by direct distillation under vacuum out of the reaction mixture or by freezing it in a solid form and separating off the liquid phase.

The novel electron deficient olefin may be stabilized during the synthesis and/or isolation procedure, and also in the isolated product to improve its shelf life. Suitable stabilizers include stabilizer packages that may contain one or more of free radical stabilizers and acidic stabilizers.

For example, free radical stabilizers include hydroquinone, pyrocatechol, resorcinol or derivatives thereof, such as hydroquinone monoethyl ether, or phenols, such as di-t-butylphenol or 2,6-di-t-butyl-p-cresol, 2,2'-methylene-bis-(4-methyl-6-t-butylphenol), bisphenol A, dihydroxydiphenylmethane, and styrenized phenols.

For example, acidic stabilizers include sulfuric acid, hydrochloric acid, sulfonic acids, such as methane, ethane or higher sulfonic acids, p-toluene sulfonic acid, phosphoric acid or polyphosphoric acids, silyl esters of strong acids, such as trialkyl chlorosilanes, dialkyl dichlorosilanes, alkyl trichlorosilanes, tetrachlorosilane, trialkyl silylsulfonic acids, trialkyl silyl-p-toluene sulfonates, bis-trialkyl silylsulfate and trialkyl silylphosphoric acid esters.

The amount of either stabilizer used to stabilize the electron deficient olefin prepared by the inventive processes is well known to those of ordinary skill in the art, and may be varied depending on the properties of the resulting composition made from the so formed electron deficient olefin.

The present invention also provides compositions of the compounds of structures I, II or III, together with a stabilizer package comprising at least one of a free radical stabilizer and an anionic stabilizer; and optionally, one or more additives selected from cure accelerators, thickeners, thixotropes, tougheners, thermal resistance-conferring agents, or plasticizers.

The cure accelerators that may be included with the inventive electron deficient olefins to form inventive compositions include calixarenes and oxacalixarenes, silacrowns, crown ethers, cyclodextrins, poly(ethyleneglycol) di(meth)acrylates, ethoxylated hydric compounds and combinations thereof.

Of the calixarenes and oxacalixarenes, many are known, and are reported in the patent literature. See e.g. U.S. Pat. Nos. 4,556,700, 4,622,414, 4,636,539, 4,695,615, 4,718, 966, and 4,855,461, the disclosures of each of which are hereby expressly incorporated herein by reference.

For instance, as regards calixarenes, those within the following structure are useful herein:

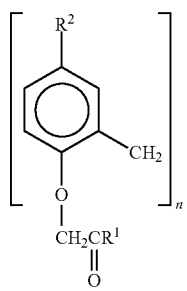

where in this connection $R^1$ is alkyl, alkoxy, substituted alkyl or substituted alkoxy; $R^2$ is H or alkyl; and n is 4, 6 or 8.

One particularly desirable calixarene is tetrabutyl tetra[2-ethoxy-2-oxoethoxy]calix-4-arene.

A host of crown ethers are known. For instance, examples which may be used herein include 15-crown-5, 18-crown-6, dibenzo-18-crown-6, benzo-15-crown-5-dibenzo-24-crown-8, dibenzo-30-crown-10, tribenzo-18-crown-6, asym-dibenzo-22-crown-6, dibenzo-14-crown-4, dicyclohexyl-18-crown-6, dicyclohexyl-24-crown-8, cyclohexyl-12-crown-4, 1,2-decalyl-15-crown-5, 1,2-naphtho-15-crown-5, 3,4,5-naphtyl-16-crown-5, 1,2-methyl-benzo-18-crown-6, 1,2-methylbenzo-5, 6-methylbenzo-18-crown-6, 1,2-t-butyl-18-crown-6, 1,2-vinylbenzo-15-crown-5, 1,2-vinyl-benzo-18-crown-6, 1,2-t-butyl-cyclohexyl-18-crown-6, asym-dibenzo-22-crown-6 and 1,2-benzo-1,4-benzo-5-oxygen-20-crown-7. See U.S. Pat. No. 4,837,260 (Sato), the disclosure of which is hereby expressly incorporated here by reference.

Of the silacrowns, again many are known, and are reported in the literature. For instance, a typical silacrown may be represented within the following structure:

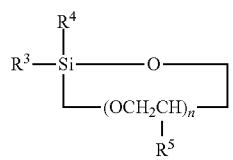

where in this connection $R^3$ and $R^4$ are organo groups which do not themselves cause polymerization of the cyanoacrylate monomer, $R^5$ is H or $CH_3$ and n is an integer of between 1 and 4. Examples of suitable $R^3$ and $R^4$ groups are R groups, alkoxy groups, such as methoxy, and aryloxy groups, such as phenoxy. The $R^3$ and $R^4$ groups may contain halogen or other substituents, an example being trifluoropropyl. However, groups not suitable as $R^4$ and $R^5$ groups are basic groups, such as amino, substituted amino and alkylamino.

Specific examples of silacrown compounds useful in the inventive compositions include:

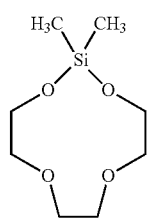

dimethylsila-11-crown-4;

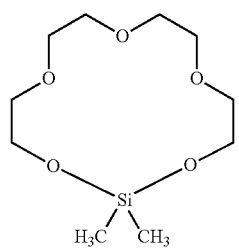 [SMILES: C[Si]1(C)OCCOCCOCCOCCO1]

dimethylsila-14-crown-5;

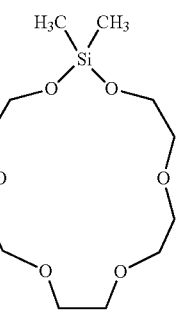

and dimethylsila-17-crown-6.

See e.g. U.S. Pat. No. 4,906,317 (Liu), the disclosure of which is hereby expressly incorporated herein by reference.

Many cyclodextrins may be used in connection with the present invention. For instance, those described and claimed in U.S. Pat. No. 5,312,864 (Went), the disclosure of which is hereby expressly incorporated herein by reference, as hydroxyl group derivatives of an α-, β- or γ-cyclodextrin which is at least partly soluble in the cyanoacrylate would be appropriate choices for use herein as the first accelerator component.

For instance, poly(ethylene glycol) di(meth)acrylates suitable for use herein include those within the following structure:

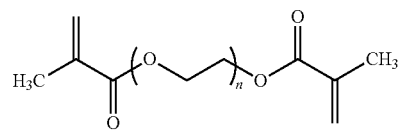

where n is greater than 3, such as within the range of 3 to 12, with n being 9 as particularly desirable. More specific examples include PEG 200 DMA (where n is about 4), PEG 400 DMA (where n is about 9), PEG 600 DMA (where n is about 14), and PEG 800 DMA (where n is about 19), where the number (e.g., 400) represents the average molecular weight of the glycol portion of the molecule, excluding the two methacrylate groups, expressed as grams/mole (i.e., 400 g/mol). A particularly desirable PEG DMA is PEG 400 DMA.

And of the ethoxylated hydric compounds (or ethoxylated fatty alcohols that may be employed), appropriate ones may be chosen from those within the following structure:

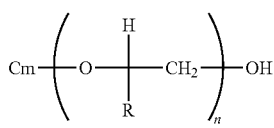

where $C_m$ can be a linear or branched alkyl or alkenyl chain, m is an integer between 1 to 30, such as from 5 to 20, n is an integer between 2 to 30, such as from 5 to 15, and R in this connection may be H or alkyl, such as $C_{1-6}$ alkyl.

Commercially available examples of materials within the above structure include those offered under the DEHYDOL tradename from Henkel KGaA, Dusseldorf, Germany, such as DEHYDOL 100.

When used, the cure accelerator should be included in the compositions in an amount within the range of from about 0.01% to about 10% by weight, with the range of about 0.1 to about 0.5% by weight being desirable, and about 0.4% by weight of the total composition being particularly desirable.

Other additives may be included with the inventive electron deficient olefins to form inventive compositions to confer additional physical properties, such as improved shock resistance, thickness (for instance, polymethyl methacrylate), thixotropy (for instance fumed silica), color, and enhanced resistance to thermal degradation [for instance, maleimide compounds such as N,N'-meta-phenylene bismaleimide (see U.S. Pat. No. 3,988,299 (Malofsky)), certain mono, poly or hetero aromatic compounds characterized by at least three substitutions on an aromatic ring thereof, two or more of which being electron withdrawing groups (see U.S. Pat. No. 5,288,794 (Attarwala)), certain quinoid compounds (see U.S. Pat. No. 5,306,752 (Attarwala)), certain sulfur-containing compounds, such as an anhydrosulfite, a sulfoxide, a sulfite, a sulfonate, a methanesulfonate or a p-toluenesulfonate (see U.S. Pat. No. 5,328,944 (Attarwala)), or certain sulfur-containing compounds, such as a sulfinate, a cyclic sultinate naphthosultone compound substituted with at least one strong electron withdrawing group at least as strongly electron withdrawing as nitro (see U.S. Pat. No. 5,424,343 (Attarwala)), and alkylating agents such as polyvinyl benzyl chloride, 4-nitrobenzyl chloride, and combinations thereof, silylating agents, and combinations thereof (see U.S. Pat. No. 6,093,780 (Attarwala)), the disclosures of each of which are hereby incorporated herein by reference. Such additives therefore may be selected from certain acidic materials (like citric acid), thixotropy or gelling agents, thickeners, dyes, thermal degradation resistance enhancers, and combinations thereof. See e.g. U.S. patent application Ser. No. 11/119,703 and U.S. Pat. Nos. 5,306,752, 5,424,344 and 6,835,789, the disclosures of each of which are hereby incorporated herein by reference.

These other additives may be used in the inventive compositions individually in an amount from about 0.05% to about 20%, such as about 1% to 15%, desirably 5% to 10% by weight, depending of course on the identity of the additive. For instance, and more specifically, citric acid may be used in the inventive compositions in an amount of 5 to 500 ppm, desirably 10 to 100 ppm.

Of course, the molecular design of the inventive electron deficient olefins may render it less desirable to include one or more these additives with the inventive electron deficient olefins to form inventive compositions.

The present invention further provides compositions of the inventive compounds, together with a cyanoacrylate, a methylidene malonate or combinations thereof.

More specifically, the cyanoacrylate used in combination with the inventive compounds is one within structure IV:

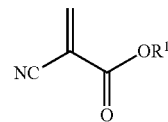

where in this connection $R^1$ is selected from $C_{1-16}$ alkyl, alkoxyalkyl, cycloalkyl, alkenyl (such as allyl), alkynyl, arylalkyl, aryl, or haloalkyl groups.

The cyanoacrylate with structure IV is selected from methyl cyanoacrylate, ethyl-2-cyanoacrylate, propyl cyanoacrylates, butyl cyanoacrylates, octyl cyanoacrylates, allyl cyanoacrylate, β-methoxyethyl cyanoacrylate and combinations thereof.

The methylidene malonate used in combination with the inventive compounds is one within structure V:

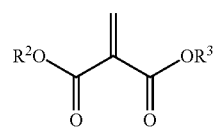

where in this connection $R^2$ and $R^3$ are each independently selected from $C_{1-16}$ alkyl, alkoxyalkyl, cycloalkyl, alkenyl, aralkyl, aryl, allyl or haloalkyl groups.

The present invention further provides compositions of certain of the compounds of structure I, together with a coreactant, such as one selected from epoxides (such as cycloaliphatic epoxies), episulfides, oxetanes, thioxetanes, dioxolanes, dioxanes, isocyanates, maleimides, oxazolines, (meth)acrylates, acrylamides, cyanoacrylates, methylidene malonates or vinyl ethers. Particularly desirable compounds within structure I for this purpose include

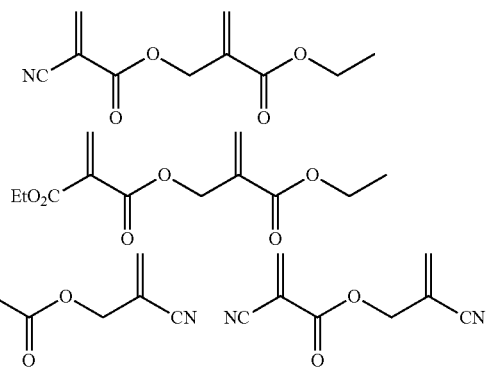

The following examples are intended to illustrate but in no way limit the present invention.

EXAMPLES

Example 1

PRIMENE 81-R imine was prepared by reaction of PRIMENE 81-R amine with a stoichiometric equivalent of paraformaldehyde and removal of water of condensation. All imines formed were distillable liquids and existed in stable monomeric imine forms as confirmed by $^1$H NMR 60 MHz (CDCl$_3$) 2H s (br) 7.45 ppm and FTIR (1650 cm$^{-1}$).

Example 2

PRIMENE 81-R iminium-MSA was prepared from PRIMENE 81-R imine by adding dropwise with stirring methane sulfonic acid at ice water bath temperature, yielding a pale yellow iminium salt.

Example 3

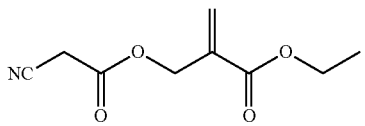

A

To a stirring mixture of cyanoacetic acid (90 g, 1.05 mol), ethyl 2-hydroxylmethyl acrylate (130 g, 1.0 mol), p-toluene sulfonic acid (500 mg) and hydroquinone (200 mg), was added toluene (150 mL), and the mixture was refluxed at a temperature of 150° C. to azeotropically remove water.

After cooling, the reaction product was washed consecutively with 30% brine and water. The organic layer was dried over anhydrous sodium sulfate, filtered and the solvent removed by rotary evaporator. The crude reaction product was purified by vacuum distillation (120-126° C./0.2 mbar), with the ester of structure A (102 g, 0.52 mol) isolated in a 52% yield. $^1$H NMR (60 MHz, CDCl$_3$): δ 6.39 (s, 1H), 5.89 (s, 1H), 4.90 (s, 2H), 4.28 (q, J=6.0 Hz, 2H), 3.50 (s, 2H), 1.32 (t, J=6.0 Hz, 3H); FT-IR (film): 2983.3, 2935.3, 2264.3, 1753.6, 1719.7, 1640.0, 1448.3, 1368.2, 1310.3, 1177.0, 1027.1, 817.2 cm$^{-1}$; GC/MS (EI) m/z (%): 198 (2) [M$^+$+H], 152 (40), 129 (25), 101 (38), 85 (100), 83 (45), 68 (80).

Example 4

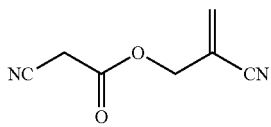

B

To a stirring solution of 2-hydroxymethylacrylonitrile (21 g, 0.25 mole) and cyanoacetic acid (20.5 g, 0.24 mole) in dry THF (0.5 l), was added a solution of dicarbodiimide ("DCC") (51.6 g, 0.25 mole) in dry THF (100 mL) over a period of time of 30 minutes at a temperature of 0° C. The reaction mixture was stirred overnight at room temperature and the solid material that formed was filtered off and washed with dry THF. The THF was removed in vacuo, the residue dissolved in dichloromethane and the solution passed through a pad of flash silica gel (200 g). The product obtained was purified additionally by precipitation with diethyl ether from its solution in dichloromethane furnishing 30.5 grams of the ester, B in a 81% yield. $^1$H NMR (250 MHz, CDCl$_3$): δ 3.58 (s, 2H), 4.80 (m, 2H), 6.13 (m, 1H), 6.19 (m, 1H); $^{13}$C NMR (62.9 MHz, CDCl$_3$): δ 24.4, 64.7, 112.6, 116.0, 116.8, 135.0, 162.4.

Example 5

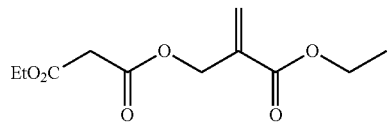

C

To a stirring mixture of monoethyl malonate (5.1 g, 38.6 mmol), ethyl 2-hydroxylmethyl acrylate (5.02 g, 3.86 mmol), PTSA (50 mg) and hydroquinone (50 mg), was added toluene (50 mL) and the mixture was refluxed at a temperature of 150° C. to azeotropically remove water.

After cooling, the reaction product was washed consecutively with 30% brine and water, and the organic layer was dried over anhydrous sodium sulfate, filtered and the solvent removed by rotary evaporator. The crude reaction product was purified by vacuum distillation (98-100° C./0.1 mbar) and the ester, C was isolated in 80% yield. $^1$H NMR (60 MHz, CDCl$_3$): δ 6.36 (s, 1H), 5.87 (s, 1H), 4.89 (s, 2H), 4.05-4.41 (m, 4H), 3.43 (s, 2H), 1.19-1.42 (m, 6H); FT-IR (film): 2984.7, 2908.6, 1735.3 (br), 1640.5, 1513.6, 1447.6, 1332.2, 1145.4, 1031.7, 817.2 cm-1; GC/MS (EI) m/z (%): 245 (2) [M$^+$+H], 226 (2), 199 (20), 153 (20), 129 (70), 115 (100), 101 (40), 85 (45), 43 (65).

Example 6

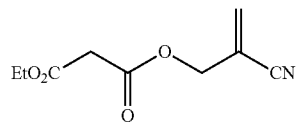

D

To a stirring mixture of monoethyl malonate (10.18 g, 77 mmol), ethyl 2-hydroxylmethyl acrylonitrile (7.67 g, 92 mmol), conc. H$_2$SO$_4$ (3 drops) and hydroquinone (1.0 g), was added toluene (50 mL) and the mixture was refluxed at a temperature of 150° C. to azeotropically remove water.

After cooling, the reaction product was washed consecutively with 30% brine and water, and the organic layer was dried over anhydrous sodium sulfate, filtered and the solvent removed by rotary evaporator. The crude reaction product was purified by vacuum distillation (86-88° C./0.05 mbar) and 7.5 g, 38 mmol of the ester, D was isolated in 49% yield. $^1$H NMR (60 MHz, CDCl$_3$): δ 6.10 (s, 2H), 4.75 (s, 2H), 4.20 (q, J=6.6 Hz, 2H), 3.47 (s, 2H), 1.34 (t, J=6.6 Hz, 3H); FT-IR (film): 3118.1, 2986.9, 2909.0, 2230.0, 1736.0, 1629.3, 1447.3, 1371.1, 1147.8, 1033.0, 959.6 cm$^{-1}$; GC/MS (EI) m/z (%): 197 (2) [M$^+$], 170 (40), 152 (100), 125 (10), 115 (50), 107 (15), 87 (25), 79 (45), 66 (90), 53 (40), 43 (60).

Example 7

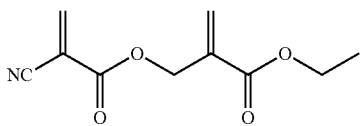
E

To a stirring mixture of PRIMENE 81-R iminium-MSA (5.86 g, 20 mmol) and cyanoacetate, A (g, 20 mmol), was added 10 mg of hydroquinone and degassed for a period of time of 5 minutes at room temperature. Immediately thereafter, the degassed stirring mixture was vacuum distilled (0.2 mbar) at a temperature of 200° C. The cyanoacrylate ester, E was collected as a colourless oil (60% purity by GC, 36% yield). $^1$H NMR (60 MHz, CDCl$_3$): δ 7.01 (s, 1H), 6.58 (s, 1H), 6.36 (s, 1H), 5.88 (s, 1H), 4.95 (s, 1H), 4.27 (q, J=6.6 Hz, 2H), 1.30 (t, J=6.6 Hz, 3H); FT-IR (film): 3125.4 (C=C), 2937.7, 2875.0, 2238.3 (CN), 1723.8 (b, s, CO), 1641.6 (C=C), 1389.2, 1310.6, 1155.5, 1026.7, 803.6 cm$^{-1}$.

Example 8

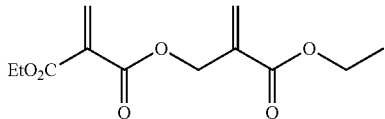
F

To a stirring mixture of PRIMENE 81-R iminium-MSA (2.93 g, 10 mmol) and the triester, C (2.44 g, 10 mmol), was added 10 mg of hydroquinone and degassed for a period of time of 5 minutes at room temperature. Immediately thereafter, the degassed stirring mixture was vacuum distilled (0.1 mbar) at a temperature of 200° C. The triester, F was collected as a colourless oil (1.7 g, 110-120° C./0.1 mbar, 43% purity by GC, 28% yield). GC/MS shows the sample is a mixture of monomer and acetate (1:1.3); $^1$H NMR (60 MHz, CDCl$_3$): δ 6.51 (s, 1H), 6.34 (s, 2H), 5.86 (s, 1H), 4.94 (s, 1H), 4.39-4.04 (m, 4H), 1.42-1.18 (m, 6H); FT-IR (film): 2984.0, 2908.7, 1731.5, 1640.6, 1400.5, 1330.5, 1272.1, 1191.5, 1144.1, 1029.3, 813.1 cm$^{-1}$.

Example 9

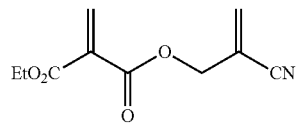
G

To a stirring mixture of PRIMENE 81-R iminium-MSA (2.93 g, 10 mmol) and the diester nitrile, D (1.97 g, 10 mmol), was added 10 mg of hydroquinone and degassed for a period of time of 5 minutes at room temperature. Immediately thereafter, the degassed stirring mixture was vacuum distilled (0.1 mbar) at a temperature of 200° C. The diester nitrile, G was collected as a colourless oil (1.7 g, 94-104° C./0.25-0.35 mbar, 80% purity by GC, 65% yield). $^1$H NMR (60 MHz, CDCl$_3$): δ 6.62 (s, 2H), 6.12 (s, 2H), 4.81 (s, 2H), 4.26 (q, J=6.0 Hz, 2H), 1.33 (t, J=6.0 Hz, 3H); FT-IR (film): 3118.4, 2985.8, 2229.9, 1736.1, 1628.7, 1407.3, 1371.9, 1331.0, 1191.8, 1030.2, 805.9 cm$^{-1}$.

Example 10

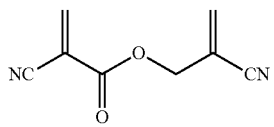
H

To a stirring mixture of PRIMENE 81-R iminium-MSA (2.93 g, 10 mmol) and the dinitrile ester, B (1.50 g, 10 mmol), was added 10 mg of hydroquinone and degassed for a period of time of 5 minutes at room temperature. Immediately thereafter, the degassed stirring mixture was vacuum distilled (0.2 mbar) at a temperature of 200° C. The dinitrile ester, K was collected as a colourless oil (0.96 g, 140-160° C./0.2-0.3 mbar, 43% purity by NMR, 25% yield). The sample was determined to contain 2-hydroxylmethyl acrylonitrile. $^1$H NMR (60 MHz, CDCl$_3$): δ 7.04 (s, 1H), 6.64 (s, 1H), 6.12 (s, 2H), 4.82 (s, 2H); FT-IR (film): 3124.9, 2960.9, 2874.6, 2229.5, 1745.0, 1678.1, 1528.9, 1284.3, 1177.4, 955.0, 802.5 cm$^{-1}$.

The table below shows the starting intermediate, the resulting electron deficient olefin, the purity of the resulting electron deficient olefin and the yield in which some of the electron deficient olefins described above were obtained.

TABLE

| Intermediate | Electron Deficient Olefin | Purity by GC (%) | Yield (%) |
|---|---|---|---|
| NC-CH₂-C(O)-O-CH₂-C(=CH₂)-C(O)-O-Et | NC-C(=CH₂)-C(O)-O-CH₂-C(=CH₂)-C(O)-O-Et | 60 | 36 |
| EtO₂C-CH₂-C(O)-O-CH₂-C(=CH₂)-C(O)-O-Et | EtO₂C-C(=CH₂)-C(O)-O-CH₂-C(=CH₂)-C(O)-O-Et | 43 | 28 |

TABLE-continued

| Intermediate | Electron Deficient Olefin | Purity by GC (%) | Yield (%) |
|---|---|---|---|
| EtO₂C—C(=O)—O—CH₂—C(=CH₂)—CN (α-H) | EtO₂C—C(=CH₂)—C(=O)—O—CH₂—C(=CH₂)—CN | 80 | 65 |
| NC—CH₂—C(=O)—O—CH₂—C(=CH₂)—CN | NC—C(=CH₂)—C(=O)—O—CH₂—C(=CH₂)—CN | 43 | 25 |

What is claimed is:

1. One or more compounds selected from the group consisting of

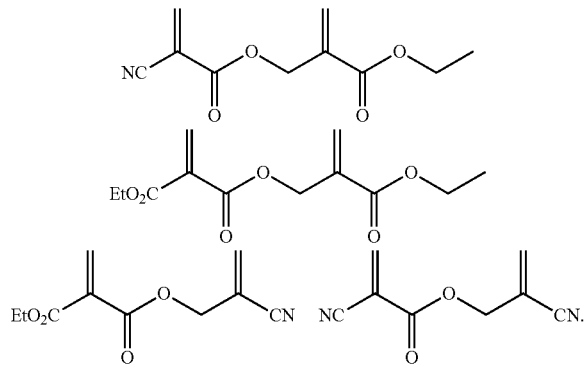

2. A composition comprising:
(a) or more compounds of claim 1;
(b) a stabilizer package comprising at least one of a free radical stabilizer and an anionic stabilizer; and
(c) optionally, one or more additives selected from the group consisting of cure accelerators, thickeners, thixotropes, tougheners, thermal resistance-conferring agents, and plasticizers.

3. The composition of claim 2, further comprising a coreactant.

4. The composition of claim 3, wherein the coreactant is a member selected from the group consisting of epoxides, episulfides, oxetanes, thioxetanes, dioxolanes, dioxanes, isocyanates, maleimides, oxazolines, (meth)acrylates, acrylamides, cyanoacrylates, methylidene malonates, vinyl ethers and combinations thereof.

5. The composition of claim 4, wherein the cyanoacrylate is within structure IV:

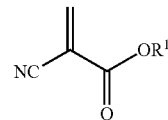

IV wherein in this connection $R^1$ is selected from $C_{1-16}$ alkyl, alkoxyalkyl, cycloalkyl, alkenyl, alkynyl, arylalkyl, aryl, or haloalkyl groups.

6. The composition of claim 4, wherein the cyanoacrylate is selected from methyl cyanoacrylate, ethyl-2-cyanoacrylate, propyl cyanoacrylates, butyl cyanoacrylates, octyl cyanoacrylates, allyl cyanoacrylate, β-methoxyethyl cyanoacrylate and combinations thereof.

* * * * *